(12) United States Patent
Larsen et al.

(10) Patent No.: US 8,530,244 B2
(45) Date of Patent: Sep. 10, 2013

(54) METHODS AND MATERIALS FOR AMPLIFICATION OF A SIGNAL IN AN IMMUNOASSAY

(75) Inventors: Gustavo Larsen, Denton, NE (US); Raffett Velarde Ortiz, Lincoln, NE (US)

(73) Assignee: Terapia Celular, L'N, Inc., Denton, NE (US)

( * ) Notice: Subject to any disclaimer, the term of this patent is extended or adjusted under 35 U.S.C. 154(b) by 405 days.

(21) Appl. No.: 12/244,538

(22) Filed: Oct. 2, 2008

(65) Prior Publication Data

US 2009/0203053 A1 Aug. 13, 2009

Related U.S. Application Data

(60) Provisional application No. 60/976,973, filed on Oct. 2, 2007.

(51) Int. Cl.
*G01N 21/76* (2006.01)
(52) U.S. Cl.
USPC ............ 436/172; 436/518; 436/536; 436/164
(58) Field of Classification Search
USPC .................................. 436/518, 536, 164, 172
See application file for complete search history.

(56) References Cited

U.S. PATENT DOCUMENTS

| | | | | |
|---|---|---|---|---|
| 5,593,843 A | * | 1/1997 | Malick et al. | 435/7.1 |
| 6,395,302 B1 | * | 5/2002 | Hennink et al. | 424/489 |
| 6,616,946 B1 | * | 9/2003 | Meier et al. | 424/489 |
| 2004/0014073 A1 | * | 1/2004 | Trau et al. | 435/6 |
| 2007/0141726 A1 | * | 6/2007 | Ying et al. | 436/525 |
| 2007/0161015 A1 | * | 7/2007 | Zheng et al. | 435/6 |
| 2008/0272331 A1 | * | 11/2008 | Mohapatra et al. | 252/70 |
| 2009/0297448 A1 | * | 12/2009 | Yan et al. | 424/9.1 |

FOREIGN PATENT DOCUMENTS

DE    EP 99111334.1    * 6/1999

* cited by examiner

*Primary Examiner* — Melanie Y Brown
(74) *Attorney, Agent, or Firm* — Howard & Howard Attorneys PLLC

(57) ABSTRACT

Ultrafine particles are provided having a core region that has a signal amplifying molecule and a shell region that surrounds the core region. The shell region has at least one antibody affixed to its surface that is specific for at least one antigen. Alternatively, the ultrafine particles may entrap the signal amplifying molecule within its matrix and may also have antibodies affixed to its surface for molecular recognition. Ultrafine particles are also provided having a matrix component that includes a signal amplifying molecule and at least one antibody specific for the antigen or biomaterial. The ultrafine particles of the present disclosure may be used in assays for the detection, including quantification, of one or more antigens present in a biological sample.

14 Claims, 3 Drawing Sheets

METHODS AND MATERIALS FOR AMPLIFICATION OF A SIGNAL IN AN IMMUNOASSAY

CROSS REFERENCE TO RELATED APPLICATIONS

This application claims priority to U.S. application Ser. No. 60/976,973, filed on Oct. 2, 2007, which is hereby incorporated by reference in its entirety.

STATEMENT OF GOVERNMENT INTEREST

This disclosure was made with Government support under contract no. DE-FG02-05ER84326. The Government has certain rights in the present disclosure.

FIELD

The present disclosure relates generally to ultrafine particles comprising a core region that comprises a signal amplifying molecule and a shell region that surrounds the core region and comprises at least one antibody affixed to its surface specific for at least one antigen or biomaterial. Alternatively, the ultrafine particles may entrap the signal amplifying molecule within its matrix and may also have antibodies affixed to its surface for molecular recognition. The ultrafine particles of the present disclosure may be used in assays for the detection, including quantification, of at least one antigen present in a biological sample.

BACKGROUND

The enzyme-linked immunosorbent assay (ELISA), is a technique commonly used to detect disease markers in body fluids of humans and animals (J. R. Crowther (1995) "Elisa: Theory and Practice", Totowa, N.J.; Humana Press). Such disease markers, generally referred to as antigens, are identified via capture on a surface with the aid of a surface-bound antibody that is highly selective toward molecular recognition and formation of a chemical complex with the said antigen, followed by a quantitative chemical analysis sequence.

In an ELISA, antigen that is captured by a specific antibody in the form of a surface-bound complex may be detected and quantified by means of an analytical chemistry protocol (see, e.g., FIG. 1). For example, a micro-well plate array may be used (101) with a primary antibody attached to the surface of the plate (102) that selectively recognizes and attaches to the antigen (103). The signal amplification sequence may start by selectively attaching a secondary antibody (104) (which is said to be "enzyme-linked" i.e., has an enzyme (e.g., horseradish peroxidase) attached to it, 105) and that recognizes the exposed portions of the antigen molecule that are left free after antigen attachment to the surface-bound primary antibody. The enzyme may be a catalyst capable of converting substrates into detectable products (e.g., colored products). Thus, a solution containing an adequate substrate may be added to the micro-wells having the surface-bound polymolecular complex consisting of species 102 through 104. After an incubation period, the amount of captured antigen may be determined by quantifying the amount of converted substrate.

Despite the fact that enzymes, for example horseradish peroxidase, are capable of converting roughly 1,000,000 substrate molecules into their color signal-emitting products per second, there are at least two limitations in the current art. First, the synthesis of the secondary antibody-enzyme complex may be laborious, costly or simply be impractical or impossible to carry out in certain cases. Second, a secondary antibody-enzyme complex only carries one signal-amplifying molecule (e.g., an enzyme) per single surface-captured antigen molecule. Furthermore, chemical interferences can affect the biochemical reaction. As such, the ratio of signal-amplifying molecule to antigen (e.g., the stoichiometric signal-amplifying molecule:antigen ratio) is one and results in an intrinsic biochemical limit for signal amplification. It is thus desirable to devise an ELISA antigen detection system that does not rely on the biochemical synthesis of a secondary antibody-enzyme complex.

SUMMARY

The present disclosure provides ultrafine particles for amplifying a signal produced in an immunoassay. Pursuant to an embodiment of the present disclosure, ultrafine particles are disclosed. The ultrafine particles may include at least one species of a signal amplifying molecule. The particles may also include an antibody affixed to its surface and specific for one or more antigens. The signal amplifying molecule may be entrapped within the particles. Alternatively, the ultrafine particles may include a core region that comprises a signal amplifying molecule and a shell region that surrounds the core region and comprises at least one antibody affixed to its surface specific for at least one antigen. Such ultrafine particles may be used to amplify at least one signal produced in an immunoassay.

The present disclosure provides ultrafine particles for detection of an antigen. The ultrafine particles may include at least one signal amplifying molecule entrapped within a matrix of the particle. Alternatively, the particles may include a core region that comprises a signal amplifying molecule and a shell region that surrounds the core region. The particles may further include at least one antibody specific for the antigen affixed to its surface.

In an embodiment, the particle has a shape that is substantially spheroidal, substantially tubular, substantially ellipsoidal, or combinations thereof. In an embodiment, the particle has a diameter of about 10 to about 50,000 nanometers.

In an embodiment, the particles include magnetic particles embedded in its surface. One example of magnetic particles is magnetite 1 to 10 nm in diameter. Where the particle has core and shell regions, the shell region may include the magnetic particles. In an embodiment, the particle may be porous. Where the particle has core and shell regions, the shell region may be porous.

In an embodiment, the signal amplifying molecule is a quantum dot, magnetic, radioactive, ultra violet sensitive, infrared sensitive, ultrasound sensitive or combinations thereof.

In an embodiment, the signal amplifying molecule is an enzyme. In an embodiment, the signal amplifying molecule is horseradish peroxidase, β-D-galactosidase (β-D-Gal), alkaline phosphatase or combinations thereof.

In an embodiment, the signal generating molecule is 3,3',5,5'-tetramethylbenzidine, para-nitrophenyl phosphate, p-nitrophenyl-β-D-galactosidase or combinations thereof. Other signal generating molecules may include chromogens or fluorogens, such as, but not limited to, 2,2' Azinodi 3-Ethyl Benzthiazoline Sulfonic Acid (ABST).

In an embodiment, the present disclosure also provides methods for amplifying a signal for biomaterials such as DNA or RNA.

In another embodiment, the present disclosure also provides methods for amplifying a signal in an immunoassay by contacting a biological sample with at least one antigen with one or more ultrafine particles. The particles may contain a signal amplifying molecule embedded within a matrix of the particle and may have at least one antibody affixed to its surface that is specific for at least one antigen. Alternatively, the particles may include a core region and a shell region. The core region may include one or more signal amplifying molecules. The shell region that surrounds the core region may include at least one antibody affixed to its surface that is specific for the one or more antigens. The method may further include adding a signal generating molecule to the contacted sample that reacts with the signal amplifying molecule. Reaction of the signal generating molecule with the signal amplifying molecule generates an amplified signal.

In an embodiment, the methods may further include incubating the signal generating molecule with the signal amplifying molecule. In some embodiments, the methods may further include obtaining the sample from a subject.

In an embodiment, a primary antibody specific for the antigen is bound to a solid surface. In an embodiment, the solid surface is a microtiter plate.

In an embodiment, the antibody is a secondary antibody specific for the antigen.

In an embodiment, the signal amplifying molecule is a quantum dot, magnetic, radioactive, ultra violet sensitive, infrared sensitive, ultrasound sensitive or combinations thereof.

In an embodiment, the signal amplifying molecule is an enzyme. In an embodiment, the signal amplifying molecule is horseradish peroxidase, β-D-galactosidase (β-D-Gal), alkaline phosphatase or combinations thereof.

In an embodiment, the signal generating molecule is 3,3', 5,5'-tetramethylbenzidine, para-nitrophenyl phosphate, p-nitrophenyl-β-D-galactosidase or combinations thereof. Other signal generating molecules may include chromogens or fluorogens, such as, but not limited to, 2,2' Azinodi 3-Ethyl Benzthiazoline Sulfonic Acid (ABST).

In yet another embodiment, the present disclosure also provides assays for detecting an antigen in a biological sample by contacting a biological sample with at least one antigen with one or more ultrafine particles. The particles may contain a signal amplifying molecule embedded within the particle and may have at least one antibody affixed to its surface that is specific for at least one antigen. Alternatively, the particles may include a core region and a shell region. The core region includes a signal amplifying molecule and the shell region that surrounds the core region includes at least one secondary antibody affixed to its surface that is specific for the one or more antigens. The assays may further include adding a signal generating molecule to the contacted sample that reacts with a signal amplifying molecule to generate a signal and detecting the signal produced by the signal generating molecule reaction with the signal amplifying molecule.

In an embodiment, the assay may further include quantifying the amount of signal detected. In an embodiment, the assay may further include incubating the signal generating molecule with the signal amplifying molecule. In an embodiment, the assay may further include obtaining the sample from a subject.

In an embodiment, a primary antibody specific for the antigen is bound to a solid surface. In an embodiment, the solid surface is a microtiter plate.

In an embodiment, the signal generating molecule is in a solution.

In an embodiment, the signal detected is a color change. In an embodiment, the signal detected is magnetic, radioactive, UV, IR, ultrasonic or combinations thereof.

In an embodiment, the particle may be porous. In an embodiment where the particle includes a core and a shell region, the shell region may be porous.

In an embodiment, the assay may further include removing ultrafine particles that are not bound to the antigen. In further embodiments, the ultrafine particles that are not bound to the antigen are removed with a magnetic rod. In further embodiments, the ultrafine particles that are not bound to the antigen are removed by centrifugation. In further embodiments, the ultrafine particles that are not bound to the antigen are removed by filtration.

In an embodiment, the signal amplifying molecule is a quantum dot, magnetic, radioactive, ultra violet sensitive, infrared sensitive, ultrasound sensitive or combinations thereof.

In an embodiment, the signal amplifying molecule is an enzyme. In an embodiment, the signal amplifying molecule is horseradish peroxidase, β-D-galactosidase (β-D-Gal), alkaline phosphatase or combinations thereof.

In an embodiment, the signal generating molecule is 3,3', 5,5'-tetramethylbenzidine, para-nitrophenyl phosphate, p-nitrophenyl-β-D-galactosidase or combinations thereof. Other signal generating molecules may include chromogens or fluorogens, such as, but not limited to, 2,2' Azinodi 3-Ethyl Benzthiazoline Sulfonic Acid (ABST).

In an embodiment, the biological sample is a biological fluid, a tissue or a cell.

In still yet another embodiment, the present disclosure provides methods for screening a subject for a disease or disorder characterized by the expression of an antigen. The methods include obtaining a biological sample from a subject, contacting the biological sample with one or more ultrafine particles. The particles may contain a signal amplifying molecule embedded within the particle and may have at least one antibody affixed to its surface that is specific for at least one antigen. Alternatively, the particles may include a core region and a shell region. The core region includes a signal amplifying molecule and the shell region that surrounds the core region includes at least one secondary antibody affixed to its surface that is specific for the one or more antigens. The methods further include adding a signal generating molecule to the contacted biological sample that reacts with the signal amplifying molecule to generate a signal, and detecting the signal produced by the signal generating molecule reaction with the signal amplifying molecule. In an embodiment, the subject has the disease or disorder when the antigen is detected. In an embodiment, the disease or disorder is cancer.

In an embodiment, the methods may comprise quantifying the amount of signal detected. In an embodiment, the methods may comprise incubating the signal generating molecule with the signal amplifying molecule.

In an embodiment, the biological sample is a tissue, cell, fluid or combination thereof.

In an embodiment, a primary antibody specific for the antigen is bound to a solid surface. In an embodiment, the solid surface is a microtiter plate.

In an embodiment, the signal generating molecule is in a solution. In an embodiment, the signal detected is a color change.

In an embodiment, the particle may be porous. In an embodiment where the particle includes a core and a shell region, the shell region may be porous.

In an embodiment, the methods include removing particles that are not bound to the antigen. In an embodiment, the ultrafine particles that are not bound to the antigen are removed with a magnetic rod. In an embodiment, the ultrafine particles that are not bound to the antigen are removed by centrifugation. In an embodiment, the ultrafine particles that are not bound to the antigen are removed by filtration.

In an embodiment, the signal amplifying molecule is a quantum dot, magnetic, radioactive, ultra violet sensitive, infrared sensitive, ultrasound sensitive or combinations thereof. In an embodiment, the signal amplifying molecule is an enzyme. In an embodiment, the signal amplifying molecule is horseradish peroxidase, β-D-galactosidase (β-D-Gal), alkaline phosphatase or combinations thereof.

The signal generating molecule is 3,3',5,5'-tetramethylbenzidine, para-nitrophenyl phosphate, p-nitrophenyl-β-D-galactosidase or combinations thereof. Other signal generating molecules may include chromogens or fluorogens, such as but not limited to 2,2' Azinodi 3-Ethyl Benzthiazoline Sulfonic Acid (ABST).

In another embodiment, the present disclosure provides immunoassay kits for detection of one or more antigens in a biological sample. The kit includes a container having one or more ultrafine particles. The particles may contain a signal amplifying molecule embedded within the particle and may have at least one antibody affixed to its surface that is specific for at least one antigen. Alternatively, the particles may include a core region and a shell region. The core region includes a signal amplifying molecule and the shell region that surrounds the core region includes at least one secondary antibody affixed to its surface that is specific for the one or more antigens. The kit also includes instructions for detecting the at least one antigen.

Additional features and advantages are described herein, and will be apparent from the following Detailed Description and the figures.

DETAILED DESCRIPTION

Ultrafine particles are provided that comprise a matrix component, wherein the matrix component includes a signal amplifying molecule embedded therein. The particles may also include at least one antibody specific for the antigen or biomaterial affixed to its surface. Alternatively, the ultrafine particle may include a shell component that has one or more antibodies specific for one or more antigens of interest affixed and/or embedded in its surface and a core component that carries a signal-amplifying molecule. Surprisingly, it has been discovered that these ultrafine particles are capable of making antibody-enzyme ratios greater than one. The ultrafine particles can be used to indirectly bind a signal amplifying molecule to an antigen without compromising the ability of a secondary antibody to bind the surface-bound primary antibody-antigen complex. Notably, these ultrafine particles may be used to amplify one or more signals produced in an immunoassay.

Ultrafine Particles

The present disclosure provides ultrafine particles useful for the detection of one or more antigens in a biological sample. The particles may contain a signal amplifying molecule embedded within the particle and may have at least one antibody affixed to its surface that is specific for at least one antigen. Alternatively, the ultrafine particles may comprise a core region that comprises a signal amplifying molecule and a shell region that surrounds the core region and comprises at least one antibody affixed to its surface specific for one or more antigens. The particles may comprise any shape known including, but not limited to, substantially spheroidal, substantially tubular, substantially ellipsoidal or combinations thereof. However, the skilled artisan will immediately appreciate that the particles may have any shape, or may even be irregularly shaped. Further, the particles may not be independent particles but may link to each other as beads in a continuous chain-like structure. The particles may also form clusters of at least two particles linked together. Such ultrafine particles may be used to amplify one or more signals produced in an immunoassay.

Figure 2:
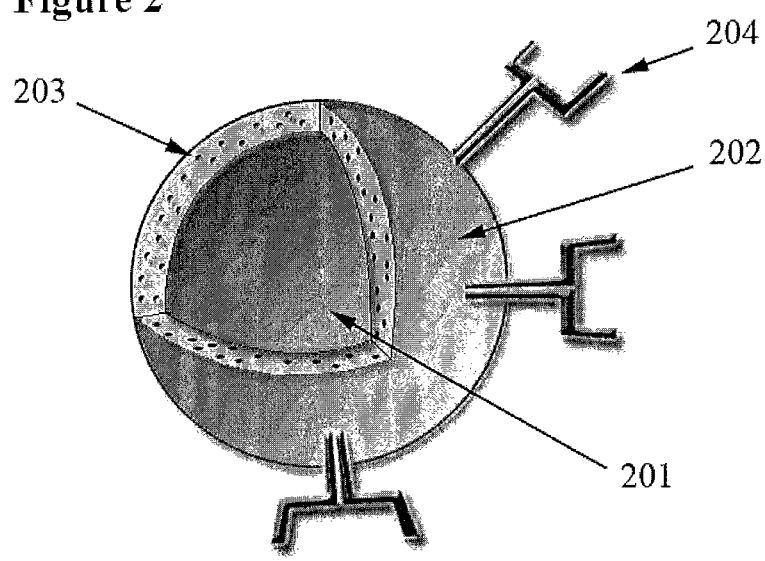
FIG. 2 depicts an ultrafine particle of the present disclosure comprising a core 201 and shell 202 component.

In an embodiment (referred to herein as Embodiment 1), the ultrafine particle has distinctive core and shell regions, as illustrated in FIG. 2. The core (201) may be a solution comprising an enzyme (e.g., horseradish peroxidase) or any other signal-amplifying chemical molecule, or combinations thereof. The shell (202) has at least one secondary antibody embedded and/or attached to its surface. Optionally, the shell may contain magnetic nanoparticles (203) embedded in its matrix. In FIG. 2, the secondary antibody (204) located at the shell of the ultrafine particle need not be in molecular proximity and/or chemically attached to a signal-amplifying molecule such as, but not limited to, horseradish peroxidase. The core-shell ultrafine particle of Embodiment 1 may be designed for antigen capture and subsequent attachment to the surface-bound primary antibody of an ELISA analysis sequence. The shell may be designed to release the core contents after contact with the solution containing the signal-generating substrate. The core-shell ultrafine particle may also be designed to have a stoichiometric ratio of core-encapsulated signal-amplifying molecule (whether or not of enzymatic origin) to shell-embedded and/or shell surface-attached secondary antibody much larger than one, unlike standard secondary antibody-signal amplifying molecular complexes.

Figure 1:
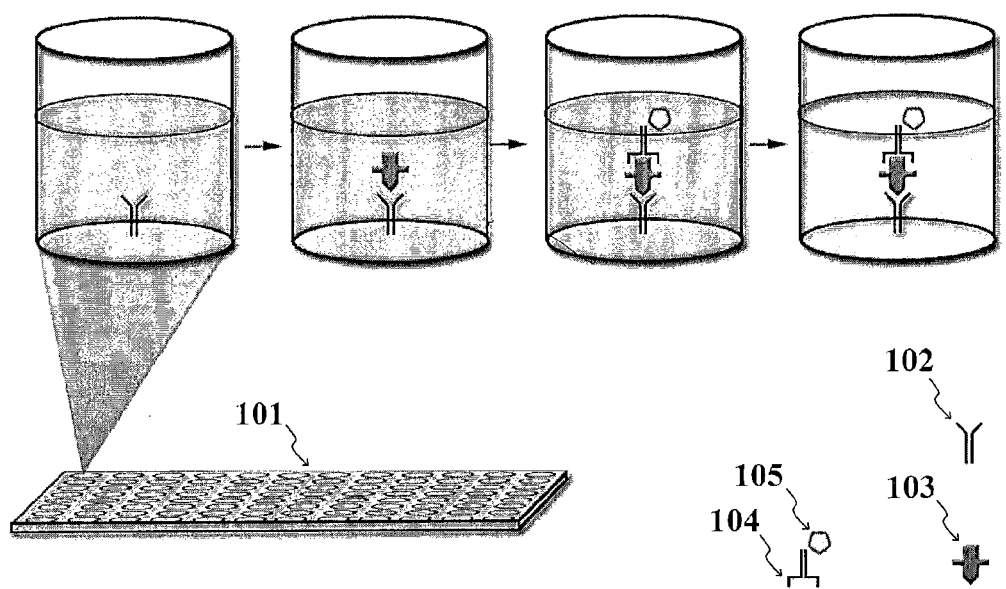
FIG. 1 shows an exemplary ELISA for the capture and detection of an antigen.

In another embodiment (referred to herein as Embodiment 2), the ultrafine particles do not have distinctive core and shell regions. Rather, the signal-amplifying molecule (whether or not of enzymatic origin) are entrapped or "matrix-encapsulated" within the major component of the particles. The particles may have at least one type of embedded and/or surface-attached secondary antibody, and they may also be designed to have a stoichiometric ratio of matrix-encapsulated signal-amplifying molecule (whether or not of enzymatic origin) to embedded and/or surface-attached secondary antibody much larger than one, unlike the standard secondary antibody/signal-amplifying molecular complexes in the conventional ELISA sequence shown in FIG. 1. Optionally, the particles may contain magnetic nanoparticles, quantum dots or combinations thereof embedded in their matrix. In Embodiment 2, the sequence of capture, detection and quantification of antigen follows procedures similar to those described in FIG. 3. Furthermore, just as in Embodiment 1, the amplifying molecule content may be released via ultrafine particle dissolution after contact with the solution having the substrate for electromagnetic radiation change. Since signal detection may not be limited to visual color changes, the ultrafine particles may contain features which provide electromagnetic signaling such as but not limited to magnetic, radioactive, UV, IR, and ultrasound-sensitive materials.

In yet another embodiment (referred to herein as Embodiment 3), the ultrafine particles are designed in the form of core-shell particles, with the shell made porous and not necessarily dissolvable in the solution having the substrate for signal change generation. The shell may have at least one secondary antibody embedded and/or attached to its surface for antigen capture, and subsequent attachment of the ultrafine particle to the surface-bound primary antibody anchored onto the concave-up surface of the micro-well (see, e.g., FIG. 3). Optionally, the particles may contain magnetic nanoparticles, quantum dots or combinations thereof. The porosity of the shell, such as its average pore diameter, is designed so as to allow passage of the signal-generating molecule into the core of the particle (where the signal-amplifying molecule reside) after contact with its solutions, and also to allow for the resulting signal-generating product or products to diffuse out of the particles. One requirement for such porous shell particles is that signal-amplifying molecule such as, but not limited to, horseradish peroxidase be large enough to be unable to diffuse out of the ultrafine particles through the shell pores, for shelf-life and storage purposes. Therefore, in Embodiment 3, and unlike Embodiments 1 and 2, there is no need for total or partial dissolution of the ultrafine particles to unleash the action of signal-amplifying molecules onto signal-generating molecules.

In another embodiment (referred to herein as Embodiment 4) the ultrafine particles are designed not to have well-defined core and shell regions. As in Embodiment 2, the signal-amplifying molecule is matrix-encapsulated within the ultrafine particle. In Embodiment 4 the matrix of the ultrafine particle may be made porous and insoluble in the liquids of the micro-wells. The porosity of the matrix may be designed so as to permit transport of signal-generating substrates and their products in and out of the ultrafine particles, but not release of the signal-amplifying molecule. The use of ultrafine particles in Embodiment 4 would be essentially the same as that of ultrafine particles in Embodiment 3.

Ultrafine particles may also be prepared as described above but without the signal-amplifying molecule. Instead, by way of nonlimiting example a core-shell or matrix-encapsulated signal-emitting molecule may replace a signal-amplifying molecule, including, for example horseradish peroxidase. On attachment of such ultrafine particle to the surface-bound primary antibody-antigen complex, detection of a signal does not require addition of a signal-generating substrate because the surface-bound particles themselves would already yield a signal.

Ultrafine particles may be designed by any method known in the art. Such methods include, but not limited to, two-fluid electrospray (Larsen et al. (2003) *J. Amer. Chem. Soc.* 125: 1154-1155), emulsion polymerization (Schork et al. (2005) *Adv. Polym. Sci.* 175: 129-255), emulsion evaporation (Lorenceau et al. (2005) *Langmuir* 21:9183-9186), coacervation (Calvo et al. (1997) *J. Appl. Polym. Sci.* 63:125-132), and spray drying (Tewa-Tagne et al. (2007) *Eur. J. Pharm. Sci.* 30:124-135).

Immunoassays

The present disclosure provides assays for detecting an antigen in a biological sample. In an exemplary method, a biological sample is contacted with one or more antigens with one or more ultrafine particles comprising a core region and a shell region, wherein the core region comprises a signal amplifying molecule and the shell region that surrounds the core region comprises at least one secondary antibody affixed to its surface that is specific for the one or more antigens. The methods further include adding a signal generating molecule to the contacted sample that reacts with the one or more signal amplifying molecules to generate a signal, and detecting the signal produced by the signal generating molecule reaction with the signal amplifying molecule.

The term "detecting" is used in the broadest sense to include both qualitative and quantitative measurements of a target molecule. In one aspect, the detecting method as described herein is used to identify the mere presence of an antigen in a biological sample. In another aspect, the method is used to test whether an antigen in a sample is at a detectable level. In yet another aspect, the method can be used to quantify the amount of an antigen in a sample and further to compare the an antigen levels from different samples.

Figure 3:
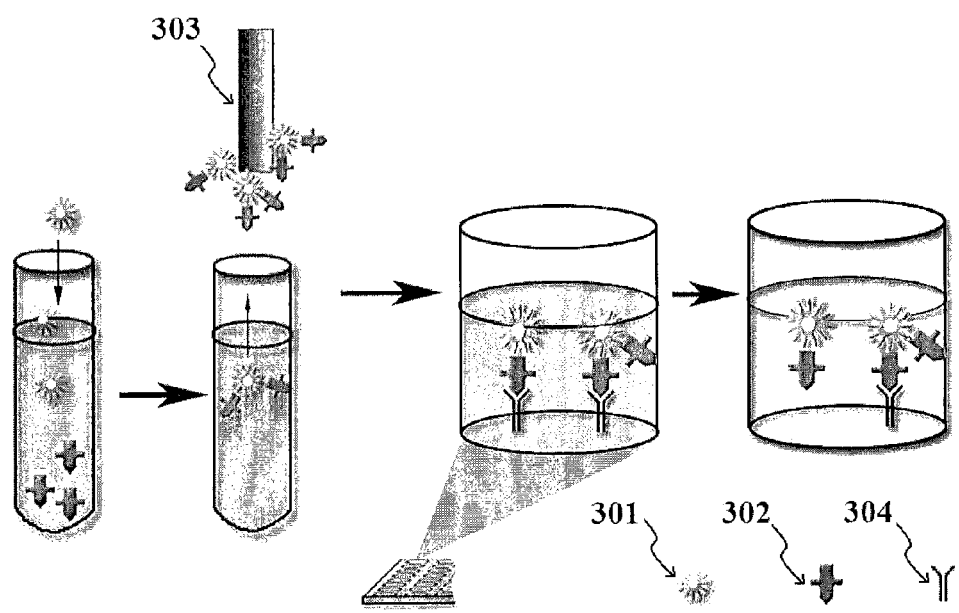
FIG. 3 shows the capture and detection of antigen with an ultrafine particle of the present disclosure.

An ELISA sequence for capturing, detecting and quantifying the desired antigen using an ultrafine particle is depicted in FIG. 3. The process starts by contacting the ultrafine particles (301) with a fluid sample containing the antigen (302). Since the ultrafine particles have the secondary antibody at their surface, as shown in FIG. 2, a substantial fraction of the antigen in the fluid sample may be captured by the ultrafine particles. The ultrafine particle-antigen adducts are then separated out of the fluid sample. As a nonlimiting example, if the ultrafine particles are made magnetically responsive, such as by loading them with magnetic nanoparticles, a magnetic rod (303) may be used to remove them from the fluid sample. Other ultrafine particle separation methods such as, but not limited to, centrifugation and filtration may be used. If, for example, the magnetic rod is sheathed with a glass rod, the ultrafine particle-antigen adducts may be released into the contents of micro-wells having surface-bound primary antibodies (304) by rinsing the glass rod sheath with a liquid after the magnetic rod had been removed from it. Ultrafine particle-antigen adducts collected via centrifugation or filtration can also be released into the contents of micro-wells having surface-bound primary antibodies. The surface-bound primary antibodies capture the ultrafine particle-antigen adducts in a fashion similar to conventional sandwich ELISA.

The signal amplification process starts by adding a solution of a signal-generating molecule to the micro-wells. If the signal-amplifying molecule carried by the ultrafine particles is an enzyme oxidation catalyst such as horseradish peroxidase, the signal-generating molecule may be 3,3',5,5'-tetramethylbenzidine. Other signal generating molecules may include chromogens or fluorogens, such as, but not limited to, 2,2' Azinodi 3-Ethyl Benzthiazoline Sulfonic Acid (ABST). To detect and amplify a signal, the chemical action of the signal-amplifying molecule upon the signal-generating molecule needs to be unleashed. In Embodiment 1, the signal-amplifying molecule is in the core of the ultrafine particle. If, in this embodiment, both ultrafine particle shell and solution of the signal-generating molecule are formulated so as to effect dissolution of the shell during the so-called incubation period, the ultrafine particle core contents are released into the liquid volume of the micro-wells. In this embodiment, the amount of signal-amplifying molecule in the core of the ultrafine particles is made as large as possible, and as permitted by solubility of the said signal-amplifying molecule in the core fluid, and/or by the ultrafine particle manufacturing parameters. Furthermore, in this embodiment the stoichiometric ratio of signal-amplifying molecule in the core of the ultrafine particles to secondary antibody contained in the shell of the ultrafine particles is made as much larger than unity as permitted by the ultrafine particle manufacturing method. Upon release of the signal-amplifying molecule into the liquid in the micro-wells, the signal generation and amplification processes are initiated.

Examples of enzyme (signal amplifying molecule)-substrate (signal generating molecule) combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase), fluorogenic substrate 4-methylumbelliferyl-p-β-galactosidase or combinations thereof. Numerous other enzyme-substrate combinations are available to those skilled in the art (see, e.g., U.S. Pat. Nos. 4,275,149 and 4,318,980). Other signal generating molecules may include chromogens or fluorogens, such as but not limited to 2,2' Azinodi 3-Ethyl Benzthiazoline Sulfonic Acid (ABST).

The solid phase used for immobilization may be any inert support or carrier that is essentially water insoluble and useful in immunometric assays, including supports in the form of, e.g., surfaces, particles, porous matrices, etc. Examples of commonly used supports include small sheets, Sephadex, polyvinyl chloride, plastic beads, and assay plates or test tubes manufactured from polyethylene, polypropylene, polystyrene, and the like including 96-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are suitably employed for capture reagent immobilization In a preferred embodiment the immobilized capture reagents are coated on a microtiter plate, and in particular the preferred solid phase used is a multi-well microtiter plate that can be used to analyze several samples at one time. The most preferred is a microtest 96-well ELISA plate such as that sold as Nune Maxisorb or Immulon.

The solid phase may be coated with the pre-mixed capture reagents as defined above, which may be linked by a non-covalent or covalent interaction or physical linkage as desired techniques for attachment include those described in U.S. Pat. No. 4,376,110 and the references cited therein. If covalent, the plate or other solid phase may be incubated with a cross-linking agent together with the capture reagent under conditions well known in the art such as for one hour at room temperature.

Commonly used cross-linking agents for attaching the pre-mixed capture reagents to the solid phase substrate include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates capable of forming cross-links in the presence of light.

If plates are utilized (e.g., 96-well plates), they are coated with the mixture of capture reagents (typically diluted in a buffer such as 0.05 M sodium carbonate by incubation for at least about 10 hours, more preferably at least overnight, at temperatures of about 4-20° C., more preferably about 4-8° C., and at a pH of about 8-12, more preferably about 9-10, and most preferably about 9.6. If shorter coating times (1-2 hours) are desired, one can use 96-well plates with nitrocellulose filter bottoms (Millipore MULTISCREEN™) or coat at 37° C. The plates may be stacked and coated long in advance of the assay itself, and then the assay can be carried out simultaneously on several samples in a manual, semi-automatic, or automatic fashion, such as by using robotics.

The coated plates may then be treated with a blocking agent that binds non-specifically to and saturates the binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, preferably about 1.5 to 3 hours.

A biological sample to be analyzed may be diluted at about 5-15%, preferably about 10%, by volume. Buffers that may be used for dilution for this purpose include (a) PBS containing 0.5% BSA, 0.05% TWEEN 20™ detergent (P20), 0.05% PROCLIN™ 300 antibiotic, 5 mM EDTA, 0.25% Chaps surfactant, 0.2% beta-gamma globulin, and 0.35M NaCl; (b) PBS containing 0.5% BSA, 0.05% P20, and 0.05% PROCLIN™ 300, pH 7; (c) PBS containing 0.5% BSA, 0.05% P20, 0.05% PROCLIN™ 300, 5 mM EDTA, and 0.35 M NaCl, pH 6.35; (d) PBS containing 0.5% BSA, 0.05% P20, 0.05% PROCLIN™ 300, 5 mM EDTA, 0.2% beta-gamma globulin, and 0.35 M NaCl; and (e) PBS containing 0.5% BSA, 0.05% P20, 0.05% PROCLIN™ 300, 5 mM EDTA, 0.25% Chaps, and 0.35 M NaCl Buffer.

The conditions for incubation of one or more antigens and one or more antibodies specific for the antigens are selected to maximize sensitivity of the assay and to minimize dissociation. The incubation may be accomplished at fairly constant temperatures, ranging from about 0° C. to about 40° C., preferably from about 36 to 38° C. to obtain a less variable, lower coefficient of variant (CV) than at, e.g., room temperature. The time for incubation depends primarily on the temperature, being generally no greater than about 10 hours to avoid an insensitive assay. The incubation time may be from about 0.5 to 3 hours, and more preferably 1.5-3 hours at 36-38° C. to maximize binding of to capture reagents. The duration of incubation may be longer if a protease inhibitor is added to prevent proteases in the biological fluid from degrading the one or more antigens of interest.

Examples of suitable signal amplifying molecules, include, for example moieties that may be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphiatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HPP, lactoperoxidase, or microperoxidase, biotin/avidin, biotin/streptavidin, biotin/Streptavidin-β-galactosidase with MUG, spin labels, bacteriophage labels, stable free radicals, and the like.

The amount of one or more antigens of interest may be determined by removing excess unbound nanoparticles through washing and then measuring the amount of the label using a detection method appropriate to the label, and correlating the measured amount with the amount of one or more antigens of interest in the biological sample. For example, in the case of enzymes, the amount of color developed and measured will be a direct measurement of the amount of one or more antigens of interest present. Specifically, if HRP is the label, the color is detected using the substrate OPD at 490 nm absorbance.

Immunoassays may be used for screening a subject for a disease or disorder characterized by the expression of an antigen. The method may include obtaining a biological sample from the subject, and contacting the biological sample with one or more ultrafine particles. The particles may contain a signal amplifying molecule embedded within the particle and may have at least one antibody affixed to its surface that is specific for at least one antigen. Alternatively, the particles may include a core region and a shell region. The core region includes a signal amplifying molecule and the shell region that surrounds the core region includes at least one secondary antibody affixed to its surface that is specific for the one or more antigens. The methods may further include adding a signal generating molecule to the contacted biological sample that reacts with the signal amplifying molecule to generate a signal, and detecting the signal produced by the signal generating molecule reaction with the signal amplifying molecule. The detection is performed on a subject having the disease or disorder at the time the antigen is detected. Such diseases or disorders may include cancer.

Articles of Manufacture

Articles of manufacture, including, for example kits, are provided by the present disclosure. The articles of manufacture may include a container and a label or package insert on or associated with the container. Suitable containers include, for example, bottles, vials or syringes. The containers may be formed from a variety of materials such as glass or plastic. The container holds one or more ultrafine particles of the present disclosure that may be used in an immunoassay, including for example to increase one or more detectable signals. The label or package insert may include directions for performing an immunoassay.

The kit may further include a solid support for the capture reagents, which may be provided as a separate element or on which an antibody specific for one or more antigens of interest are immobilized. Hence, the antibody specific for one or more antigens of interest in the kit may be immobilized on a solid support, or they may be immobilized on such support that is included with the kit or provided separately from the kit. The antibody specific for one or more antigens of interest may be coated on a microtiter plate. Where the amplifying molecule is an enzyme, the kit will ordinarily include substrates and cofactors required by the enzyme, and where the amplifying molecule is a fluorophore, a dye precursor that provides the detectable chromophore.

The kit also typically contains instructions for carrying out the assay as well as other additives such as stabilizers, washing and incubation buffers, and the like. The components of the kit will be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

This example demonstrates the encapsulation of a signal amplifying molecule in a biopolymeric core-shell capsule functionalized with antibodies using electrohydrodynamic forces.

In an exemplary method, encapsulation of horseradish peroxidase (HRP) in a capsule is designed following the teachings of Embodiment 1. The core fluid solution may be prepared by dissolving HRP in buffer solutions, such as PBS buffer, for example 10 mM, pH=7.4. The shell solution may be prepared by dissolving poly(lactide-co-glycolide), or PLGA, with a molecular weight between 10 kDa and 500 kDa in ethyl acetate. The lactide content in PLGA ranges between 0.1 and 99 wt %. A pegylated secondary antibody dissolved in a mixture of ethyl acetate and dimethyl sulfoxide with a volume ratio 1:1 is added to the PLGA solution. The weight percent content of PLGA in the shell solution may be between 0.01 to 10 wt %. By way of nonlimiting example, the pegylated secondary antibody can be from an antibody of CA-125, or from a cluster of differentiation, such as but not limited to CD-19 and/or CD-20. It is thus understood that the "term secondary antibody" applies to CA-125, CD-19, CD-20, and to any other antibody whether or not of proteinaceous origin.

Core-shell capsules with an average diameter between 0.050 μm and 50 μm may be madeby two-fluid electrospray. In one example of two-fluid electrospray, the core and shell fluids are made to pass through an inner tube and an outer tube, respectively, and arranged coaxially. An electrical potential difference is applied between the coaxial tubes assembly, and a particle collection surface. Characteristic internal diameters of the outer and inner tubes are in the range of 0.1 to 3.0 millimeters. Representative separation between the two-tube assembly and the collector surface are 1 to 100 cm. To make core-shell capsules in the 0.050-50 μm range using the core and shell solutions described above in this Example, applied voltages in the 1 to 20 kV range are also necessary, and fluid flow rates for the core and shell liquids between 0.005-0.50 mL/h, and 0.03-3.0 mL/h, respectively, are also necessary. Core-shell capsules with a HRP loading between 0.01 and 20% by weight of the added polymer may be made by the method described above in this Example by adjusting the concentration of the core fluid solution. Capsules with a secondary antibody loading between 5 and 100 μg per mg of the added polymer may be made by adjusting the concentration of the shell fluid solution.

Example 2

This example demonstrates the fabrication of ultrafine particles containing rhodamine 6G in a biopolymer matrix functionalized with antibodies using electrohydrodynamic forces.

In an exemplary method, particles are designed following Embodiment 2. A solution may be prepared by dissolving the poly(lactide-co-glycolide), or PLGA, with a molecular weight between 10 kDa and 500 kDa in ethyl acetate. The lactide content in PLGA ranges between 0.1 and 99 wt %. A solution containing rhodamine 6G dissolved in ethanol may be added to the PLGA solution to afford a final concentration of the chromophore between 0.1 and 100 mg/mL. A pegylated secondary antibody dissolved in a mixture of ethyl acetate and dimethyl sulfoxide with a volume ratio 1:1 is added to the PLGA solution. Particles with a secondary antibody loading between 5 and 100 μg per mg of the added polymer may be made adjusting its concentration in solution. Particles with an average diameter between 0.050 μm and 50 μm may be made by adjusting process variables as known in the art, such as single-fluid electrospray. Single-fluid electrospray is based on a single tube, rather than two. Characteristic internal diameter of the single-electrospray tube may be in the range of 0.1 to 3.0 millimeters. Representative separation between the tube and the collector surface may be 1 to 100 cm. To make particles in the 0.050-50 μm range using the solution described above, applied voltages in the 1 to 20 kV range are also necessary, and fluid flow rate of the solution between 0.003-3.0 mL/h is also necessary.

Example 3

This example demonstrates the encapsulation of rhodamine 6G in an ultrafine capsule with a shell functionalized with antibodies using water-in-oil-in-water (W-O-W) emulsion-evaporation.

In an exemplary method, poly(lactide-co-glycolide) or PLGA with a molecular weight between 10 kDa and 500 kDa is dissolved in ethyl acetate to afford a final concentration between 0.1 and 10 wt %. The lactide content in PLGA ranges between 0.1 and 99 wt %. This PLGA solution is mixed with a pegylated secondary antibody dissolved in a mixture of ethyl acetate and dimethyl sulfoxide with a volume ratio 1:1. Capsules with a secondary antibody loading between 5 and 100 Mg per mg of the added polymer may be made adjusting the concentration of the shell fluid solutions. Rhodamine 6G may be dissolved in an aqueous solution containing dimethyl sulfoxide and glycerin in a 1:1 volume ratio, respectively. This aqueous solution may be added to the solution prepared above in this Example under constant mixing and emulsified via sonication for 1 hour. The emulsion is then poured in an aqueous solution of poly(vinyl alcohol) between 1 and 10 wt % with a molecular weight between 5 kDa and 60 kDa under constant mixing and it is emulsified via sonication for 1 hour. Ethyl acetate may be evaporated off the solution at 40° C. under magnetic stirring to produce capsules with average diameters between 0.5 μm and 50 μm.

Example 4

This example demonstrates the encapsulation of horseradish peroxidase (HRP) in a biopolymeric core-shell capsule with porous walls and functionalized with antibodies using electrohydrodynamic forces.

In an exemplary method, a capsule may be designed following the teachings described in Embodiment 3. A core fluid solution may be prepared by dissolving HRP in a PBS buffer solution (10 mM, pH=7.4). A shell solution may be prepared by mixing a solution containing a pegylated secondary antibody dissolved in ethyl acetate and dimethyl sulfoxide (1:1 volume ratio) and an aged, acid-catalyzed silicon alkoxide solution. Core-shell capsules with an average diameter between 0.250 μm and 50 μm may be made by adjusting process variables as known in the art. Core-shell capsules with a HRP loading between 0.01 and 20 wt % by weight of the added polymer may be made by adjusting the concentration of the core fluid solution. Capsules with a secondary antibody loading between 5 and 100 μg per mg of the added polymer may be made adjusting the concentration of the shell fluid solutions.

Example 5

This example demonstrates the fabrication of ultrafine particles containing a FITC pegylated moiety using electrohydrodynamic forces.

In an exemplary method, a solution may be prepared by dissolving two polymers: A) poly(lactide-co-glycolide), or PLGA, with a molecular weight between 10 kDa and 500 kDa in ethyl acetate, and the lactide content in PLGA ranges between 0.1 and 99 wt %; and B) A pegylated FITC or PEG-F, with a molecular weight ranging between 1 kDa and 50 kDa. The weight percent content of PLGA and PEG-F is between 0.01 to 10 wt % for each polymer. This solution may be mixed with a solution containing a pegylated secondary antibody dissolved in a mixture of ethyl acetate and dimethyl sulfoxide with a volume ratio 1:1. Particles with a secondary antibody loading between 5 and 100 μg per mg of the added polymer may be made adjusting the concentration of the shell fluid solutions. Particles with an average diameter between 0.250 μm and 50 μm may be made by adjusting process variables as known in the art.

Example 6

This example demonstrates the encapsulation of horseradish peroxidase (HRP) in a water-in-oil-in-oil (W/O/O) emulsion.

In an exemplary method, poly(D-L lactide) or PLA with a molecular weight between 10 kDa and 500 kDa may be dissolved in dichloromethane to afford a final concentration between 0.1 and 10 wt %. HRP may be dissolved in a 1.0M phosphate buffered solution (PBS) solution with a pH between 5 and 7 to afford a final concentration of HRP between 0.001 mg/mL and 10 mg/mL. This HRP aqueous solution may be added to the PLA solution under constant mixing and homogenized using a vortexer for a time period between 1 and 10 minutes. The resulting W/O emulsion is poured under constant mixing into aqueous solution containing silicon oil at a concentration between 1 and 5% by volume. The resulting W/O/O emulsion may be poured into ethyl ether under constant mixing. The PLA capsules are recovered by filtration, washed and dried under air at room temperature. PLA capsules with an average diameter between 30 and 300 μm may be made adjusting the process variables such as, but not limited to, ratio of HRP solution to PLA solution, PLA concentration and homogenization conditions. A burst release of HRP may be triggered by addition of PBS aqueous solution containing acetone with a concentration between 1-10% by volume. The HRP released into the aqueous solution may be then detected by addition of TMB/hydrogen peroxide substrates.

Example 7

This example demonstrates the encapsulation of horseradish peroxidase (HRP) in a siloxane matrix using electrohydrodynamic forces.

In an exemplary method, a solution may be prepared by dissolving HRP in a 1.0 M phosphate buffered solution (PBS) with a pH between 5 and 7 to afford a final concentration of HRP between 0.001 mg/mL and 10 mg/mL. This aqueous solution may be mixed with an aged, acid-catalyzed siloxane sol-gel under constant mixing to produce a homogenous solution. If a precipitate forms vortex the solution until the solid re-disperses. The HRP/siloxane solution may be then electrohydrodynamically sprayed at a flow rate of 100-500 μL/h and a voltage between 5 and 10 kV. The distance between nozzle and collector may be between 5-15 cm. Particles with an average diameter between 1 μm and 50 μm may be made adjusting the process variables following the methods and procedures described in the previous Example. A burst release of HRP may be triggered by addition of PBS aqueous solution containing acetone with a concentration between 1-10% by volume. The HRP released into the aqueous solution may be then detected by addition of TMB/hydrogen peroxide substrates.

Example 8

This example demonstrates the encapsulation of horseradish peroxidase (HRP) in a siloxane core-shell capsule using electrohydrodynamic forces.

In an exemplary method, the shell fluid may be comprised of an aged, acid-catalyzed siloxane sol-gel. The core fluid is prepared by dissolving HRP in a 1.0 M phosphate buffered solution (PBS) with a pH between 5 and 7 to afford a final concentration of HRP between 0.001 mg/mL and 10 mg/mL. Core-shell capsules with an average diameter between 1 μm and 10 μm may be made from solutions such as those described above and two-fluid electrospray. In one example of two-fluid electrospray, the core and shell fluids are made to pass through an inner tube and an outer tube, respectively, and arranged coaxially. An electrical potential difference may be applied between the coaxial tubes assembly, and a particle collection surface. Characteristic internal diameters of the outer and inner tubes are in the range of 0.1 to 3.0 millimeters. Representative separation between the two-tube assembly and the collector surface are 1 to 100 cm. To make core-shell capsules in the 1 μm-10 μm range using the core and shell solutions described above, applied voltages in the 1 to 20 kV range are also necessary, and fluid flow rates for the core and shell liquids between 0.005-0.50 mL/h, and 0.03-3.0 mL/h, respectively, are also necessary. A burst release of HRP may be triggered by addition of PBS aqueous solution containing acetone with a concentration between 1-10% by volume. The HRP released into the aqueous solution may be then detected by addition of TMB/hydrogen peroxide substrates.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An ultrafine particle for detection of an antigen, the particle comprising:
    a. a core region comprising a solution comprising one or more signal amplifying molecules; and
    b. a shell region that surrounds the core region and comprises at least one antibody specific for the antigen affixed to a surface of the shell region and magnetic nanoparticles,
  wherein the ultrafine particle has a stoichiometric ratio of core-encapsulated signal-amplifying molecule to antibody greater than one.

2. The ultrafine particle of claim 1, wherein the particle comprises a shape selected from the group consisting of substantially spheroidal, substantially tubular, substantially ellipsoidal, and combinations thereof.

3. The ultrafine particle of claim 2, wherein the particle has a diameter of about 10 to about 50,000 nanometers.

4. The ultrafine particle of claim 1, wherein the signal amplifying molecule is a quantum dot.

5. The ultrafine particle of claim 1, wherein the signal amplifying molecule is selected from the group consisting of magnetic, radioactive, ultra violet sensitive, infrared sensitive, ultrasound sensitive, and combinations thereof.

6. The ultrafine particle of claim 1, wherein the signal amplifying molecule is an enzyme.

7. The ultrafine particle of claim 1, wherein the signal amplifying molecule is selected from the group consisting of horseradish peroxidase, 0-D-galactosidase ((-DGal), alkaline phosphatase, and combinations thereof.

8. The ultrafine particle of claim 1, wherein the shell region comprises one or more pores.

9. The ultrafine particle of claim 1, wherein the signal generating molecule is selected from the group consisting of 3,3',5,5'-tetramethylbenzidine, para-nitrophenyl phosphate, p-nitrophenyl-0-D-galactosidase, ABST, and combinations thereof.

10. The ultrafine particle of claim 1, wherein the shell region is designed to release the one or more signal amplifying molecules after contact with a solution containing a signal generating substrate.

11. The ultrafine particle of claim 8, wherein the one or more pores in the shell region are of a size to permit the transport of signal generating substrates and their products in and out of the ultrafine particle.

12. The ultrafine particle of claim 11, wherein the pores in the shell region are of a size that does not allow the one or more signal amplifying molecules to be transported out of the ultrafine particle.

13. The ultrafine particle of claim 8, wherein the pores in the shell region are of a size to permit the transport of the one or more signal amplifying molecules out of the ultrafine particle.

14. An ultrafine particle for detection of an antigen, the particle comprising:
    a. a core region comprising a solution that comprises one or more signal amplifying molecules; and
    b. a shell region that surrounds the core region and comprises at least two antibodies specific for the antigen affixed to a surface of the shell region and magnetic nanoparticles,
  wherein the ultrafine particle has a stoichiometric ratio of core-encapsulated signal-amplifying molecule to antibody greater than one and wherein the ultrafine particle has a diameter of about 10 to about 500 nanometers.

* * * * *